(12) United States Patent
Emmerich

(10) Patent No.: US 10,437,277 B2
(45) Date of Patent: Oct. 8, 2019

(54) FOOTSWITCH FOR A MEDICAL INSTRUMENT

(71) Applicant: Karl Storz SE & Co. KG, Tuttlingen (DE)

(72) Inventor: Bernd Emmerich, Tuttlingen (DE)

(73) Assignee: Karl Storz SE & Co. KG, Tuttlingen (DE)

(*) Notice: Subject to any disclaimer, the term of this patent is extended or adjusted under 35 U.S.C. 154(b) by 34 days.

(21) Appl. No.: 15/650,057

(22) Filed: Jul. 14, 2017

(65) Prior Publication Data
US 2018/0024586 A1 Jan. 25, 2018

(30) Foreign Application Priority Data

Jul. 19, 2016 (DE) .................. 10 2016 113 259

(51) Int. Cl.
| | | |
|---|---|---|
| *G05G 1/30* | (2008.04) | |
| *G05G 23/00* | (2006.01) | |
| *H01H 3/14* | (2006.01) | |
| *A61B 17/00* | (2006.01) | |
| *A61C 1/00* | (2006.01) | |
| *A61B 18/00* | (2006.01) | |
| *H01H 9/02* | (2006.01) | |

(52) U.S. Cl.
CPC .............. *G05G 1/30* (2013.01); *G05G 23/00* (2013.01); *H01H 3/14* (2013.01); *A61B 18/00* (2013.01); *A61B 2017/00973* (2013.01); *A61C 1/0023* (2013.01); *H01H 9/02* (2013.01); *H01H 2300/014* (2013.01)

(58) Field of Classification Search
USPC ........................................................ 248/683
See application file for complete search history.

(56) References Cited

U.S. PATENT DOCUMENTS

| | | | | | |
|---|---|---|---|---|---|
| 2,828,379 | A * | 3/1958 | Simonds | .................. | G05G 1/30 200/325 |
| 3,020,017 | A * | 2/1962 | Watson | .................. | A61G 13/12 248/205.8 |
| 5,091,656 | A * | 2/1992 | Gahn | .................. | A61C 1/0023 200/86.5 |
| 5,324,900 | A * | 6/1994 | Gonser | .................. | A61G 15/02 200/302.1 |
| 5,635,777 | A * | 6/1997 | Telymonde | .............. | H01H 3/14 200/86.5 |
| 5,983,749 | A * | 11/1999 | Holtorf | .................... | G05G 1/30 74/478 |

(Continued)

FOREIGN PATENT DOCUMENTS

DE 102013113411 A1 7/2015

*Primary Examiner* — Monica E Millner
(74) *Attorney, Agent, or Firm* — Whitmyer IP Group LLC

(57) ABSTRACT

A footswitch for a medical instrument, with a housing, and with an elastically deformable suction cup arranged in the housing, where a negative pressure is generated in the suction cup by means of an evacuation device in order to secure the housing to a floor surface. In order to create a footswitch which is suitable for a medical instrument and which, while having a simple design and being easy to handle, ensures that the footswitch is secured in a fixed position on a floor surface. The suction cup is elastically extensible via the evacuation device in order to generate the negative pressure by enlargement of the volume enclosed by the suction cup.

14 Claims, 2 Drawing Sheets

(56) References Cited

U.S. PATENT DOCUMENTS

| | | | | |
|---|---|---|---|---|
| 6,362,441 B1* | 3/2002 | Xie | G05G 1/30 | 200/81 H |
| 6,478,271 B1* | 11/2002 | Mulholland | F16B 47/00 | 248/205.8 |
| 6,637,707 B1* | 10/2003 | Gates | A47B 81/005 | 211/64 |
| 6,931,962 B2* | 8/2005 | Maurer | G05G 1/30 | 74/491 |
| 6,962,581 B2* | 11/2005 | Thoe | A61B 17/00 | 200/51.02 |
| 7,205,468 B1* | 4/2007 | Johnson | G10G 5/005 | 84/327 |
| 7,229,059 B1* | 6/2007 | Hood | B60R 11/00 | 248/205.8 |
| 7,270,357 B1* | 9/2007 | Liao | B65G 7/12 | 294/15 |
| 7,578,487 B2* | 8/2009 | Kaneda | A47B 19/002 | 248/205.8 |
| 7,628,362 B2* | 12/2009 | Song | F16B 47/003 | 248/205.5 |
| 7,690,610 B2* | 4/2010 | Ristau | F16B 47/00 | 248/205.5 |
| 7,691,097 B2* | 4/2010 | Miyazawa | A61B 1/00016 | 606/1 |
| 8,151,481 B2* | 4/2012 | Perez, Jr. | A45D 20/14 | 248/160 |
| 8,409,214 B2* | 4/2013 | Lonky | A61M 1/0031 | 606/123 |
| 8,584,997 B2* | 11/2013 | Hajianpour | F16B 47/00 | 248/205.5 |
| 2002/0137007 A1* | 9/2002 | Beerstecher | A61C 1/0023 | 433/101 |
| 2003/0047434 A1* | 3/2003 | Hanson | A61B 17/00 | 200/86.5 |
| 2004/0256529 A1* | 12/2004 | Richter | F16B 47/006 | 248/309.1 |
| 2007/0210225 A1* | 9/2007 | Carnevali | F16B 47/00 | 248/205.8 |
| 2008/0230662 A1* | 9/2008 | Takahashi | F16B 47/006 | 248/206.2 |
| 2012/0292463 A1* | 11/2012 | Burns | F16M 11/041 | 248/125.8 |
| 2012/0301844 A1* | 11/2012 | Guaragno | A61C 17/20 | 433/101 |
| 2014/0128852 A1* | 5/2014 | Gooding | A61F 9/009 | 606/4 |
| 2014/0276547 A1* | 9/2014 | Lonky | A61M 1/0066 | 604/503 |
| 2014/0363784 A1* | 12/2014 | Monty | A61C 1/0046 | 433/29 |
| 2015/0227719 A1* | 8/2015 | Ranalletta | G06F 19/00 | 141/83 |
| 2016/0025264 A1* | 1/2016 | Casagrande | F16M 11/14 | 248/205.9 |
| 2017/0066370 A1* | 3/2017 | Bowe | B60Q 1/2615 | |

* cited by examiner

FOOTSWITCH FOR A MEDICAL INSTRUMENT

TECHNICAL FIELD

The invention relates to a footswitch for a medical instrument, with a housing, and with an elastically deformable suction cup arranged in the housing, it being possible for a negative pressure to be generated in the suction cup by means of an evacuation device in order to secure the housing to a floor surface.

BACKGROUND

Footswitches are often used in medicine in order to control appliances, cameras and the like and to activate or deactivate various functions of the appliances. To ensure safe actuation of the appliances that are to be controlled, it is absolutely essential that the footswitch can be secured in a fixed position on the floor surface.

A footswitch of the type in question is known, for example, from DE 10 2013 114 411 A1. In this known footswitch, the negative pressure in the suction cup is generated by active suctioning by means of an electrically operated evacuation device. The use of the electrically operated evacuation device is very costly.

Proceeding from this, the object of the invention is to create a footswitch which is suitable for a medical instrument and which, while having a simple design and being easy to handle, ensures that the footswitch is secured in a fixed position on a floor surface.

SUMMARY

According to the invention, this object is achieved by the fact that the suction cup is elastically extensible via the evacuation device in order to generate the negative pressure by enlargement of the volume enclosed by the suction cup.

By virtue of the design of the evacuation device according to the invention, in which the suction cup is not actively evacuated and instead the enclosed volume is enlarged, it is possible to dispense entirely with valves, as a result of which a simple and cost-effective structure is possible. By virtue of the design according to the invention, there is therefore also no need for an electrically operated suctioning device for generating the negative pressure in the suction cup.

In a practical embodiment of the invention, it is proposed that the evacuation device is designed as a tensioning device engaging on the suction cup. The circumferential surface of the elastically deformable suction cup is extended via the tensioning device and, consequently, the volume enclosed by the suction cup is enlarged, which has the effect of reducing the air pressure inside the suction cup since no more air is able to flow into the suction cup from outside.

As regards the configuration of the tensioning device, the invention proposes that the tensioning device is designed as a tension rod which can be actuated via a toggle lever mounted externally on the housing.

According to a preferred embodiment of the invention, the toggle lever is designed as a two-armed toggle lever, of which the arms between them span an angle of 90° to 140°, and is mounted pivotably at a pivot axis on the housing at the contact point of the two arms. This toggle lever arranged on the housing can be easily actuated either by a foot or hand in order to fix the housing of the footswitch in a fixed position on a floor surface by generating the negative pressure in the suction cup. In addition to fixing the footswitch to the floor, it is likewise possible, for transport and/or storage purposes, to secure the footswitch to an equipment trolley via the suction cup.

The invention further proposes that the toggle lever is mounted on the tensioning device via a first arm, and the toggle lever is pivotable, via a second arm, between a starting position, in which the tensioning device is released and the suction cup untensioned, and a suction position, in which the suction cup is expanded via the tensioning device. The pivoting of the toggle lever thus has a direct effect on the suction cup and therefore on the fixing or release of the footswitch relative to the surface on which the latter stands.

To prevent accidental actuation of the toggle lever situated in the suction position and thus to prevent accidental release of the footswitch from the floor surface, the invention proposes that the second arm of the toggle lever can be fixed to the housing in the suction position actuating the tensioning device.

According to a first practical embodiment of the invention, the fixing of the second arm of the toggle lever to the housing in the suction position is effected via a magnet arranged on the housing or on the second arm of the toggle lever. The use of a magnet for fixing the toggle lever in the suction position provides for a simple and cost-effective structure which, in addition, is easy to clean.

In a second embodiment, it is proposed, according to the invention, that the pivot axis extends through a ball, which is provided with at least one plane flattening and on which the toggle lever is mounted. It is further proposed that the fixing of the toggle lever to the housing in the suction position is effected via at least one spring element, which acts on the at least one plane flattening of the ball.

Alternatively, it is of course also possible to fix the second arm of the toggle lever in the suction position via a clamping mechanism on the housing.

Finally, the invention proposes that the suction cup can be ventilated via a valve device in order to facilitate the release of the suction cup from the floor surface.

BRIEF DESCRIPTION OF THE DRAWINGS

Further features and advantages of the invention will become clear from the attached drawings in which two illustrative embodiments of a footswitch according to the invention for a medical instrument are shown only by way of example, without limiting the invention to these illustrative embodiments. In the drawings.

DETAILED DESCRIPTION

Figure 1:
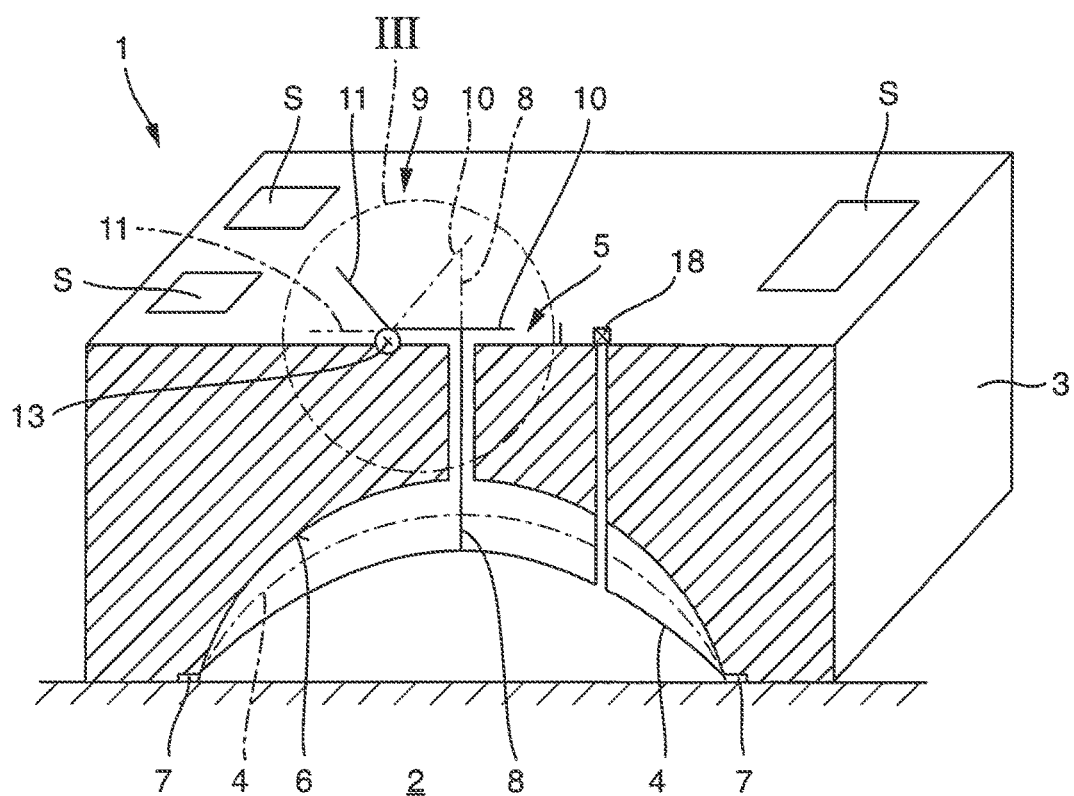
FIG. 1 shows a schematic longitudinal section through a footswitch according to the invention for a medical instrument.

FIG. 1 shows a schematic longitudinal section through a footswitch 1 for a medical instrument (not shown). Footswitches 1 are often used in medicine in order to control medical instruments, appliances, cameras and the like and to activate or deactivate various functions of the medical instruments.

To ensure safe actuation of the instruments that are to be controlled, it is absolutely essential that the footswitch 1 can be secured in a fixed position on a floor surface 2. For this purpose, it has proven useful in practice to arrange an elastically deformable suction cup 4 in a housing 3 of the footswitch 1, it being possible for a negative pressure to be generated in the suction cup 4 by means of an evacuation device 5 in order to secure the housing 3 to the floor surface 2.

By generating the negative pressure in the suction cup 4 arranged in the housing 3, the housing 3 of the footswitch 1 is pressed in a fixed position onto the floor surface 2 by means of the higher external atmospheric pressure acting on the housing 3.

The negative pressure in the suction cup 4 can be generated either by air being actively sucked out of the suction cup 4, by means of an evacuation device, or by the volume enclosed by the suction cup 4 being enlarged, which results in a reduction of the air pressure inside the suction cup 4 if no more air can flow into the suction cup 4 from the outside.

The footswitch 1 shown in FIG. 1 for a medical instrument is basically composed of the housing 3 in which a receiving space 6, open toward the floor surface 2, is formed for receiving the suction cup 4. To operate the medical instrument controllable via the footswitch 1, various switches S (not shown in any detail) are arranged on the top face of the housing.

Figure 2:
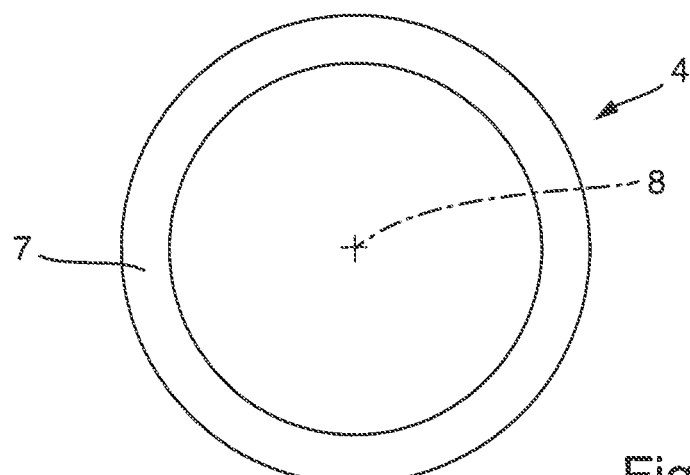
FIG. 2 shows a schematic plan view of a suction cup.

As will be seen from FIGS. 1 and 2, the hemispherically shaped suction cup 4 has a circumferential edge 7 acting as a sealing lip with respect to the housing 3. The suction cup 4 is made of an elastically deformable material, for example rubber or silicone.

In the embodiment shown, the negative pressure required for securing the housing 3 to the floor surface 2 is generated via the evacuation device 5 designed as a tensioning device 8. For this purpose, the tensioning device 8 is designed as a tension rod which engages on the suction cup 4 and via which, by application of a tensile force to the circumferential surface of the suction cup 4, the volume enclosed by the suction cup 4 is enlarged. Since no more air can flow into the suction cup 4 from the outside, on account of the circumferential edge 7 of the suction cup 4 forming a seal under the housing 3, this expansion of the suction cup 4 via the tensioning device 8 causes the generation of a negative pressure inside the suction cup 4.

In the embodiment shown, the tensioning device 8 is actuated via a toggle lever 9 which is arranged externally on the housing 3 and which is designed as a two-armed toggle lever 9, of which the arms 10 and 11 between them span an angle of 90° to 140°, and is mounted pivotably at a pivot axis 13 on the housing 3 at a contact point 12 of the two arms 10 and 11.

As will also be seen from FIG. 1, the toggle lever 9 is mounted on the tensioning device 8 via the first arm 10, and the toggle lever 9 is pivotable, via a second arm 11, between a starting position, in which the tensioning device 8 is released and the suction cup 4 untensioned, and a suction position, in which the suction cup 4 is expanded via the tensioning device 8.

In FIG. 1, the starting position in which the tensioning device 8 is released and the suction cup 4 untensioned is indicated by a solid line, whereas the suction position, in which the suction cup 4 is expanded via the tensioning device 8, and the associated position of the toggle lever 9 are shown by dot-and-dash lines.

To ensure that a substantially vertical tensile force is applied to the suction cup 4 via the tension rod of the tensioning device 8 during the pivoting of the toggle lever 9, the tension rod of the tensioning device 8 is mounted in an articulated manner both on the suction cup 4 and also on the first arm 10 of the toggle lever 9.

The footswitch 1 is released from the floor surface 2 by the toggle lever 9 being pivoted back again. As a result of the elasticity of the material of the suction cup 4, the suction cup 4 contracts to its original shape again as soon as no further tensile force is applied to the suction cup 4 via the tensioning device 8.

The contraction of the suction cup 4 causes the internal pressure inside the suction cup 4 to increase to the initial atmospheric pressure, at which point the footswitch 1 can be lifted easily again from the floor surface 2.

To prevent accidental actuation of the toggle lever 9 situated in the suction position and thus to prevent accidental release of the footswitch 1 from the floor surface 2, the second arm 11 of the toggle lever 9 can be fixed to the housing 3 in the suction position actuating the tensioning device 8.

Figure 3:
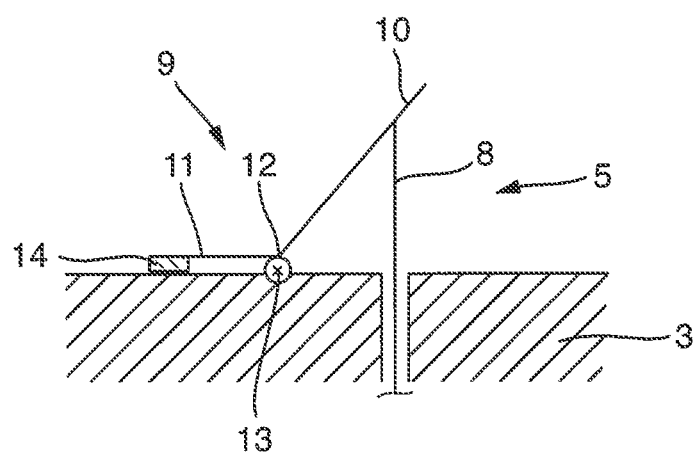
FIG. 3 shows an enlarged view of the detail III from FIG. 1, depicting a first embodiment of the toggle lever.
Figure 4:
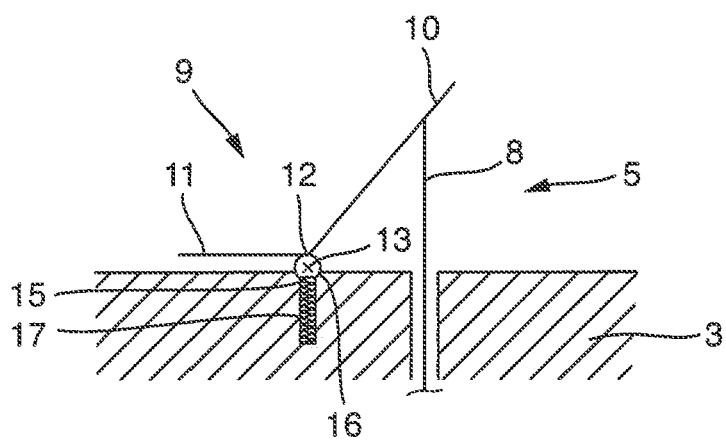
FIG. 4 shows a view according to FIG. 3, but depicting a second embodiment of the toggle lever.

FIGS. 3 and 4 show two illustrative embodiments of how the second arm 11 of the toggle lever 9 can be fixed to the housing 3 in the suction position.

In the first embodiment, shown in FIG. 3, the fixing of the second arm 11 of the toggle lever 9 to the housing 3 in the suction position is effected via a magnet 14 which is arranged on the second arm 11 of the toggle lever 9 and interacts with a magnetic reaction surface on the housing 3. Alternatively, the magnet 14 can also be arranged on or in the housing 3 and can interact with a magnetic reaction surface on the second arm 11 of the toggle lever 9.

According to the second embodiment, shown in FIG. 4, the pivot axis 13 about which the toggle lever 9 is pivotable extends through a ball 16, which is provided with at least one plane flattening 15 and on which the toggle lever 9 is mounted. In this embodiment, the fixing of the toggle lever 9 to the housing 3 in the suction position is effected via at least one spring element 17, which acts on the at least one plane flattening 15 of the ball 16.

As will be seen from FIG. 4, the spring element 17 designed as a compression spring is mounted in the housing 3 such that the housing 3, at one end of the spring element 17, forms an abutment for the spring element 17, and the free other end of the spring element 17 bears on the ball 16.

In the starting position in which the tensioning device 8 is released and the suction cup 4 is untensioned, the free end of the spring element 17 bears on the spherical outer surface of the ball 16. The spring force of the spring element 17 is of such an order that the spring element 17, when bearing on the spherical outer surface of the ball 16, does not inhibit the pivoting of the toggle lever 9.

In the pivoted suction position of the toggle lever 9, the free end of the spring element 17 now no longer bears on the spherical outer surface of the ball 16 but instead on the plane flattening 15 of the ball 16. The spring element 17 subjects this plane flattening 15 of the ball 16 to such a pressure force that accidental actuation of the toggle lever 9 located in the suction position is ruled out and, consequently, accidental release of the footswitch 1 from the floor surface 2 is ruled out.

To transfer the toggle lever 9 back to the starting position in which the tensioning device 8 is released and the suction cup 4 relaxed, a force has to be deliberately applied to the toggle lever 9 in order to pivot the latter counter to the pressure force applied by the spring element 17 to the flattening 15 of the ball 16.

Since suction cups 4 may have a tendency to remain suctioned to the floor surface 2, via the circumferential edge 7 acting as sealing lip, even after the negative pressure has been canceled, i.e. even after the toggle lever 9 has been pivoted back to the starting position and the suction cup 4 has expanded, the embodiment according to FIG. 1 has an additional valve device 18 through which the suction cup 4 can additionally be ventilated from the outside after the negative pressure has been canceled.

A footswitch 1 constructed in the manner described above and provided for a medical instrument is characterized in that, while having a simple design and being easy to handle, it ensures that the footswitch 1 is secured in a fixed position on a floor surface 2.

The invention claimed is:

1. A footswitch for a medical instrument, comprising:
a housing and an elastically deformable suction cup arranged in the housing, wherein a negative pressure is generated in the suction cup by means of an evacuation device in order to secure the housing to a floor surface,
a toggle lever which actuates the evacuation device, and
a switch engageable by a foot, wherein the switch activates or deactivates a function of the medical instrument,
wherein the suction cup is elastically extensible via the evacuation device in order to generate the negative pressure by enlargement of the volume enclosed by the suction cup.

2. The footswitch as claimed in claim 1, wherein the evacuation device is designed as a tensioning device engaging on the suction cup.

3. The footswitch as claimed in claim 2, wherein the tensioning device is designed as a tension rod which is actuatable via the toggle lever mounted externally on the housing.

4. The footswitch as claimed in claim 3, wherein the toggle lever is designed as a two-armed toggle lever, of which the arms between them span an angle of 90° to 140°, and is mounted pivotably at a pivot axis on the housing at the contact point of the two arms.

5. The footswitch as claimed in claim 4, wherein the toggle lever is mounted on the tensioning device via a first arm, and the toggle lever is pivotable, via a second arm, between a starting position, in which the tensioning device is released and the suction cup untensioned, and a suction position, in which the suction cup is extended via the tensioning device.

6. The footswitch as claimed in claim 5, wherein the second arm of the toggle lever can be fixed to the housing in the suction position actuating the tensioning device.

7. The footswitch as claimed in claim 6, wherein the fixing of the second arm of the toggle lever to the housing in the suction position is effected via a magnet arranged on the housing or on the second arm of the toggle lever.

8. The footswitch as claimed in claim 4, wherein the pivot axis extends through a ball, which is provided with at least one plane flattening and on which the toggle lever is mounted.

9. The footswitch as claimed in claim 8, wherein the fixing of the toggle lever to the housing in the suction position is effected via at least one spring element, which acts on the at least one plane flattening of the ball.

10. The footswitch as claimed in claim 1, wherein the suction cup is ventilated via a valve device.

11. The footswitch as claimed in claim 5, wherein the pivot axis extends through a ball, which is provided with at least one plane flattening and on which the toggle lever is mounted.

12. The footswitch as claimed in claim 6, wherein the pivot axis extends through a ball, which is provided with at least one plane flattening and on which the toggle lever is mounted.

13. The footswitch as claimed in claim 2, wherein the suction cup can be ventilated via a valve device.

14. The footswitch as claimed in claim 3, wherein the suction cup can be ventilated via a valve device.

* * * * *